US008233978B1

(12) United States Patent
Province et al.

(10) Patent No.: US 8,233,978 B1
(45) Date of Patent: Jul. 31, 2012

(54) METHOD AND DEVICE FOR SWITCHING BETWEEN ARRHYTHMIA PREVENTION MODES

(75) Inventors: Rose A. Province, San Jose, CA (US);
Gene A. Bornzin, Simi Valley, CA (US);
Paul A. Levine, Santa Clarita, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1637 days.

(21) Appl. No.: 10/890,538

(22) Filed: Jul. 12, 2004

(51) Int. Cl.
*A61N 1/00* (2006.01)

(52) U.S. Cl. .......................................................... 607/9

(58) Field of Classification Search ...................... 607/9
See application file for complete search history.

(56) References Cited

U.S. PATENT DOCUMENTS

| | | | | |
|---|---|---|---|---|
| 4,686,988 | A | | 8/1987 | Sholder .................... 128/419 PT |
| 4,708,142 | A | | 11/1987 | DeCote, Jr. ............. 128/419 PT |
| 4,712,555 | A | | 12/1987 | Thornander et al. ..... 128/419 PG |
| 4,729,376 | A | | 3/1988 | DeCote, Jr. ............. 128/419 PT |
| 4,788,980 | A | | 12/1988 | Mann et al. .............. 128/419 PG |
| 4,809,697 | A | | 3/1989 | Causey, III et al. ...... 128/419 PG |
| 4,940,052 | A | | 7/1990 | Mann et al. .............. 128/419 PG |
| 4,944,298 | A | | 7/1990 | Sholder .................... 128/419 PG |
| 4,944,299 | A | | 7/1990 | Silvian .................... 128/419 PG |
| 4,969,467 | A | | 11/1990 | Callaghan et al. ....... 128/419 PG |
| 5,114,949 | A | * | 5/1992 | Gueremy et al. .............. 514/293 |
| 5,144,949 | A | * | 9/1992 | Olson .............................. 607/17 |
| 5,312,445 | A | * | 5/1994 | Nappholz et al. ................. 607/9 |
| 5,350,410 | A | | 9/1994 | Kleks et al. ...................... 607/28 |
| 5,643,326 | A | * | 7/1997 | Weiner et al. ................... 607/14 |
| 6,058,328 | A | | 5/2000 | Levine et al. ................... 607/14 |
| 6,275,734 | B1 | | 8/2001 | McClure et al. ................ 607/27 |
| 6,285,907 | B1 | | 9/2001 | Kramer et al. .................... 607/9 |
| 6,292,694 | B1 | | 9/2001 | Schloss et al. .................... 607/9 |
| 6,442,429 | B1 | | 8/2002 | Hill et al. ........................ 607/14 |
| 6,519,493 | B1 | | 2/2003 | Florio et al. ...................... 607/9 |
| 7,133,721 | B1 | * | 11/2006 | Bornzin et al. ................. 607/17 |
| 7,142,917 | B2 | * | 11/2006 | Fukui .............................. 607/14 |
| 7,181,279 | B2 | * | 2/2007 | Bjorling et al. ................... 607/9 |

OTHER PUBLICATIONS

Gronefeld, G., et al., "Association Between Atrial Fibrillation and Appropriate Implantable Cardioverter Defibrillator Therapy: Results form a Prospective Study," Journal of Cardiovascular Electrophysiology, 11(11), pp. 1208-1214 (2000).
Pekarsky, V., et al., "Prevention of Recurrent Life-Threatening Ventricular Arrythmias by Temporary Cardiac Pacing," Acta Med Scand, vol. 21, pp. 95-99 (1985).
Wittkampf, F. and DeJongste, M., "Rate Stabilization by Right Ventricular Pacing in Patients with Atrial Fibrillation," PACE, vol. 9(Part II), pp. 1147-1153 (1986).

* cited by examiner

*Primary Examiner* — George Manuel
(74) *Attorney, Agent, or Firm* — Theresa Raymer; Steven M. Mitchell

(57) ABSTRACT

A device, such as an implantable cardiac device, and method for switching between arrhythmia prevention modes is disclosed. The method includes monitoring an electrocardiogram (EGM) of the heart, determining whether the heart is in a normal sinus rhythm or in an abnormal rhythm, delivering pacing pulses at a first rate to either an atrium or a ventricle when the heart is in a normal sinus rhythm, and delivering pacing pulses to a ventricle at a second rate when the heart is in an abnormal rhythm, such as an atrial arrhythmia. The first rate is selected to minimize the occurrence of premature ventricular contractions, and the second rate is selected to both minimize the occurrence of premature ventricular contractions and minimize the occurrence of premature conducted beats.

29 Claims, 6 Drawing Sheets

METHOD AND DEVICE FOR SWITCHING BETWEEN ARRHYTHMIA PREVENTION MODES

BACKGROUND OF THE INVENTION

1. Field of the Invention

The present invention relates generally to implantable cardiac devices and, more particularly, to an implantable cardiac device with the capability of switching between arrhythmia prevention modes.

2. Background Art

An implantable cardiac device is a medical device that is implanted in a patient to monitor electrical activity of the heart and to deliver appropriate electrical and/or drug therapy, as required. Implantable cardiac devices include, for example, pacemakers, cardioverters and defibrillators. The term "implantable cardioverter defibrillator" or simply "ICD" is used herein to refer to any implantable cardiac device capable of delivering therapy to prevent or terminate a fast heart rate or a tachycardia. An ICD employs a battery to power its internal circuitry and to generate electrical therapy. The electrical therapy can include, for example, pacing pulses, cardioverting pulses and/or defibrillator pulses. This is in contrast to a "pacemaker" which is an implantable device specifically intended to treat slow heart rates or bradycardia.

An ICD also provides all the features of a pacemaker. However, a pacemaker does not provide all of the therapy that can be provided by an ICD. While the term "ICD" is used throughout the specification, it is to be understood that similar techniques as described herein can be applied in a pacemaker. A pacemaker cannot initiate therapy if a tachyarrhythmia occurs, but it can stabilize the ventricular rate in the setting of atrial fibrillation and can prevent atrial and ventricular arrhythmias.

There is indirect evidence that ventricular instability during an atrial arrhythmia can be a mechanism for inducing a ventricular arrhythmia. A recent study showed that the presence of atrial fibrillation is an independent predictor of appropriate ICD therapy, with ICD therapy being 1.8 times more frequent in patients in atrial fibrillation versus patients in sinus rhythm. More information regarding this study can be found in "Association Between Atrial Fibrillation and Appropriate Implantable Cardioverter Defibrillator Therapy: Results form a Prospective Study," by Gronefeld, G, et al., Journal of Cardiovascular Electrophysiology, 11(11), pp. 1208-1214 (2000).

It has also been shown that overdrive ventricular pacing can reduce ventricular extrasystoles and arrhythmias. (See Pekarsky, V., et al., "Prevention Of Recurrent Life-Threatening Ventricular Arrythmias By Temporary Cardiac Pacing," Acta Med Scand, Vol. 21, pp. 95-99 (1985).) In addition, it has been shown that pacing the ventricle slightly over the mean intrinsic ventricular rate during atrial fibrillation can significantly reduce the number of premature conducted beats (PCBs) from the atria. (See Wittkampf, F. and DeJongste, M., "Rate Stabilization By Right Ventricular Pacing in Patients with Atrial Fibrillation," PACE, Vol. 9(Part II), pp. 1147-1153 (1986).)

What is needed is a device, such as an ICD, that takes advantage of such evidence to reduce the occurrence of arrhythmias by delivery of appropriate electrical therapy.

BRIEF SUMMARY OF THE INVENTION

For each individual patient, there is an optimum pacing rate that reduces premature ventricular contractions (PVCs) and also reduces the number of premature conducted beats (PCBs) from the atria during atrial arrhythmias. Conventional ICDs and related preventive therapy algorithms do not provide a pacing rate optimized for this purpose.

In patients with paroxysmal atrial fibrillation, there is a need for at least two modes of therapy. One therapy should be administered to the ventricle during atrial fibrillation to regularize and control the ventricular rhythm and possibly reduce ventricular ectopy, reducing the incidence of ventricular tachycardia or fibrillation. The other therapy should be provided during sinus rhythm to either the atrium or the ventricle to reduce ventricular and/or atrial extrasystoles, and potentially increase repolarization homogeneity. Further, various pacing algorithms might be utilized in the atrium to prevent atrial fibrillation and other atrial arrhythmias. Conventional ICDs and related preventive therapy algorithms do not provide this dual-mode form of prevention.

The present invention includes a device, such as an implantable cardiac device, and method for switching between arrhythmia prevention modes. The method includes monitoring the intrinsic signals inside the heart (i.e., the electrogram (EGM) of the heart), determining whether the heart is in a normal sinus rhythm or in an abnormal rhythm, delivering pacing pulses to either an atrium or a ventricle at a first rate when the heart is in a normal sinus rhythm, and delivering pacing pulses to a ventricle at a second rate when the heart is in an abnormal rhythm, such as an atrial arrhythmia. The advantage of this invention is that prevention therapy can be tailored to alleviate the symptoms and arrhythmia risk in both rhythm states. The invention, as described, involves two arrhythmia prevention modes. However, it will be appreciated by those skilled in the art that the invention can be extended to also cover three or more arrhythmia prevention modes. In addition, an arrhythmia prevention mode, depending on the underlying rhythm, may be applied to specific chambers of a heart (atrium or ventricle).

A method for pacing a heart for use in a pacing device such as an ICD with at least two pacing modes directed to reduce ventricular arrhythmias is presented, according to an embodiment of the present invention. The method includes monitoring an electrogram (EGM) of the heart, determining whether the heart is in a normal sinus rhythm or in an abnormal rhythm, delivering pacing pulses to either an atrium or a ventricle at a first rate when the heart is in a normal sinus rhythm, and delivering pacing pulses to a ventricle at a second rate when the heart is in an abnormal rhythm. In an embodiment of the present invention, the method further includes monitoring a response to the delivered pacing pulses with respect to a frequency of premature ventricular contractions (PVCs) and a frequency of premature conducted beats (PCBs).

According to an embodiment of the present invention, the pulses delivered at the first rate are delivered to an atrium, and the pulses delivered at the second rate are delivered to a ventricle. In another embodiment, the pulses delivered at the first rate are delivered to a ventricle, and the pulses delivered at the second rate are delivered to a ventricle. In a further embodiment, the pulses delivered at each rate are delivered to specified leads of a pacing device.

According to an embodiment of the present invention, the first rate and the second rate are determined from data obtained from the monitored EGM. In one embodiment, the first rate is selected to minimize the occurrence of premature ventricular contractions. The second rate is selected to both minimize the occurrence of premature ventricular contractions and minimize the occurrence of premature conducted beats.

According to an embodiment of the present invention, the method further includes continuing the monitoring of the EGM of the heart. This embodiment also includes adjusting the first rate to minimize premature ventricular contractions when delivering pacing pulses at the first rate. This embodiment further includes adjusting the second rate to minimize premature ventricular contractions and premature conducted beats when delivering pacing pulses at the second rate. In a further embodiment, a response to the adjusted rates is monitored with respect to a frequency of PVCs and a frequency of PCBs.

The embodiments of the present invention related to the device for switching between arrhythmia prevention modes include means for performing the above-described method.

Further features and advantages of the present invention as well as the structure and operation of various embodiments of the present invention are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements. Additionally, in most drawings, the leftmost digit of a reference number identifies the drawing in which the reference number first appears.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It will be apparent to one of skill in the art that the present invention, as described below, may be implemented in many different embodiments of hardware, software, firmware, and/or the entities illustrated in the figures. Any actual software and/or hardware described herein is not meant to limit the scope of the present invention. Thus, the structure, operation and behavior of the present invention will be described with the understanding that many modifications and variations of the embodiments are possible, given the level of detail presented herein.

Figure 1A:
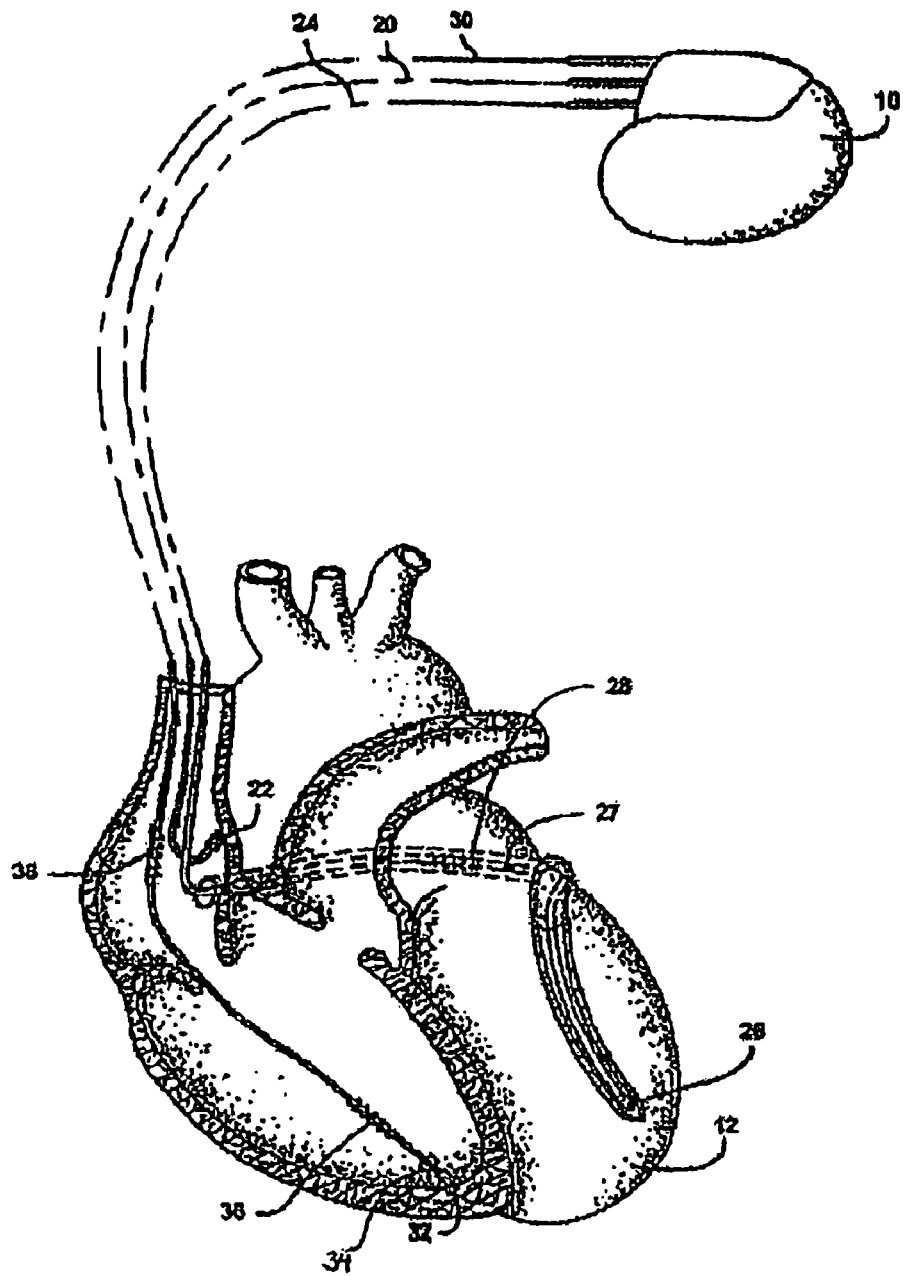
FIG. 1A is a simplified diagram illustrating an exemplary ICD in electrical communication with at least three leads implanted into a patient's heart for delivering multi-chamber stimulation and shock therapy.
Figure 1B:
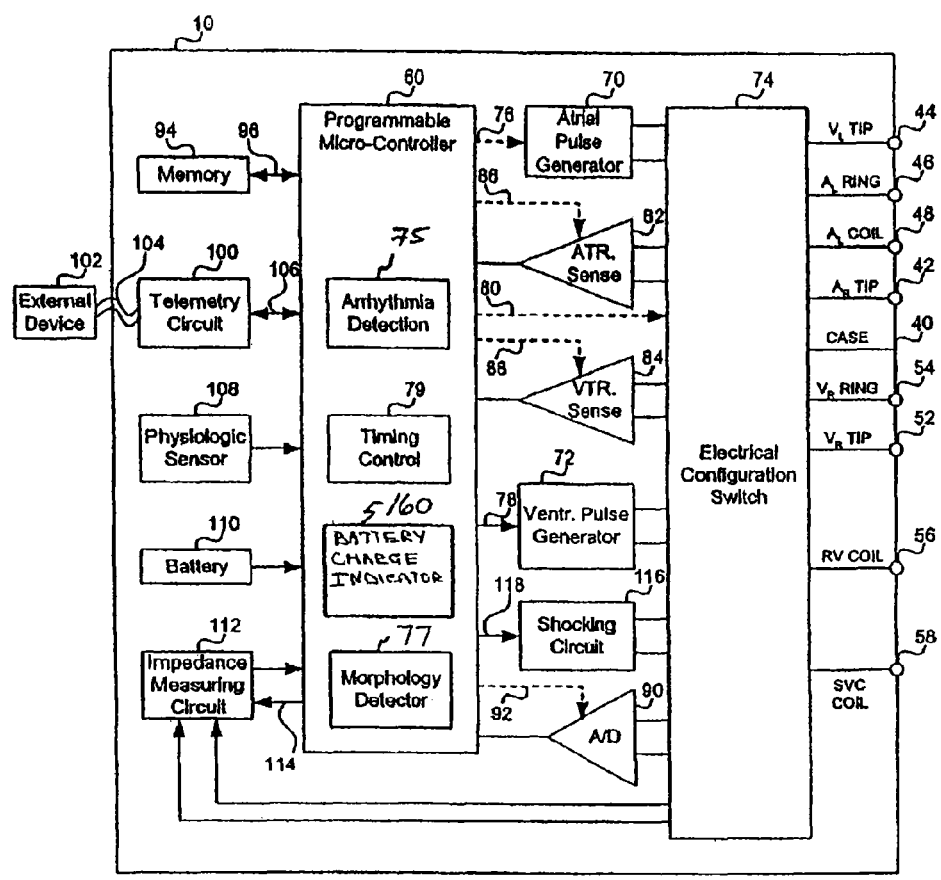
FIG. 1B is a functional block diagram of an exemplary ICD, which can provide cardioversion, defibrillation and pacing stimulation in four chambers of a heart.

Before describing the invention in detail, it is helpful to describe an example environment in which the invention may be implemented. The present invention is particularly useful in the environment of an implantable cardiac device. Implantable cardiac devices include, for example, pacemakers, cardioverters and defibrillators. The term "implantable cardioverter defibrillator" or simply "ICD" is used herein to refer to any implantable cardioverter defibrillator ("ICD") or implantable cardiac device capable of delivering therapy to prevent, manage, or terminate a tachyarrhythmia in the atrium or ventricle. FIGS. 1A and 1B illustrate such an environment.

As shown in FIG. 1A, there is an exemplary ICD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 1B shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular electrode 26, left atrial ring electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art. In specific embodiments of the present invention, microcontroller 60 performs some or all of the steps associated with the prevention therapy in accordance with the present invention.

Representative types of control circuitry that may be used with the invention include the microprocessor-based control system of U.S. Pat. No. 4,940,052 (Mann et al.) and the state-machines of U.S. Pat. Nos. 4,712,555 (Thornander et al.) and 4,944,298 (Sholder). For a more detailed description of the various timing intervals used within the ICDs and their inter-relationship, see U.S. Pat. No. 4,788,980 (Mann et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70,72, may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic sensitivity control, bandpass filtering, and a threshold detection circuit, as known in the art, to selectively sense the cardiac signal of interest. The automatic sensitivity control (ASC) enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 77 to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (DeCote, Jr.); U.S. Pat. No. 4,708,142 (DeCote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In an embodiment, ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.) in accordance with the embodiments of the present invention. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 additionally includes a battery 110 which provides operating power to all of the circuits shown in FIG. 1B. For ICD 10, which employs shocking therapy, battery 110 must be capable of operating at low current drains for long periods of time, and then be capable of providing high-current pulses (for capacitor charging) when the patient requires a shock pulse. Battery 110 must also have a predictable discharge characteristic so that elective replacement time can be detected. Accordingly, ICD 10 preferably employs lithium/silver vanadium oxide batteries, as is true for most (if not all) current devices. ICD 10 further includes a battery charge indicator circuit 160. Battery charge indicator circuit 160 monitors current drawn from battery 110 to improve prediction of when battery 110 needs replacement.

ICD 10 further includes magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that the external programmer 102 is in place to receive or transmit data to microcontroller 60 through telemetry circuit 100.

As further shown in FIG. 1B, ICD 10 is shown as having an impedance measuring circuit 112 which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

With the description of an example environment, such as an ICD, in mind, features of the present invention are described in more detail below.

As stated in the Background section, there is indirect evidence that ventricular instability during an atrial arrhythmia can be a mechanism for inducing a ventricular arrhythmia. As also stated in the Background section, it has also been shown that overdrive ventricular pacing can reduce ventricular extrasystoles and arrhythmias. In addition, it has been shown that pacing the ventricle slightly over the mean intrinsic ventricular rate during atrial fibrillation can significantly reduce the number of premature conducted beats (PCBs) from the atria.

There is an optimum pacing rate that reduces premature ventricular contractions (PVCs) and also reduces the number of premature conducted beats (PCBs) from the atria during atrial arrhythmias. In patients with paroxysmal atrial fibrillation, there is a need for at least two modes of preventive therapy. One therapy should be administered to the ventricle during atrial fibrillation to regularize the ventricular rhythm and possibly reduce ventricular ectopy. Another therapy should be provided during sinus rhythm to either the atrium or the ventricle to reduce atrial or ventricular extrasystoles respectively, and potentially increase repolarization homogeneity of the respective chamber. Further, various pacing algorithms might be utilized in the atrium to prevent atrial fibrillation and other atrial arrhythmias.

With the background in mind, a method of pacing for use in a pacing device such as an ICD with at least two pacing modes directed to reduce ventricular arrhythmias will now be described, according to an embodiment of the present invention. For example, one pacing mode is to be used during a normal sinus rhythm, and another pacing mode is to be used during an abnormal rhythm, such as an atrial arrhythmia. Optimum pacing rates for use during each mode are calculated. The prevention therapy is tailored to alleviate symptoms and other arrhythmia risk in both rhythm states.

There are many ways that a multi-mode system such as this can be implemented. In addition, there are many possible feedback parameters that can be used to control the output of a pacing device. The feedback parameters and how they are used to control device output are dependent on which mode the device is currently in (e.g., a normal sinus mode, or an abnormal arrhythmia mode). For example, possible feedback parameters include, but are not limited to, the number of PCBs from the atria, the mean ventricular rate during atrial fibrillation, PVCs (including frequency, QRS morphology being either from a single focus (monomorphic) or from multiple foci (polymorphic) occurrence, and repetitive cycles such as doublet and triplet occurrence), and cardiac output.

Based on feedback parameters, possible prevention therapy outputs include, but are not limited to, vagal stimulation and pacing at a physiologic rate. Pacing at a preventive rate may be slightly above the intrinsic heart rate, for example, and may be accomplished at the septum or at multiple ventricular sites, for example. In patients with chronic or paroxysmal atrial fibrillation, without heart failure or increased R wave width, the pacing may be at a unique location such as the interventricular septum to minimize the detrimental effects that are being recognized with RV apical pacing. In patients with heart failure or increased R wave width, it may be beneficial to pace biventricularly. The site of stimulation is dependent on where the leads are placed at the time of implantation. With multisite stimulation and total independent control of each lead, it may be possible to designate to which lead or leads the output should be delivered in order to achieve preventive therapy.

According to embodiments of the present invention, the number of PCBs and the number of PVCs are used as feedback for pacing rate optimization during normal sinus rhythm and during an abnormal rhythm, such as atrial fibrillation. This embodiment is described in more detail below with reference to the accompanying figures. Note that, according to embodiments of the present invention, the number of PVCs is also used as a tripper to initiate or turn on pacing.

Figure 2A:
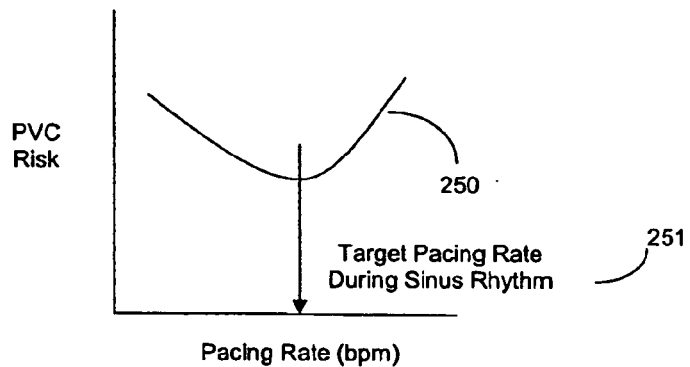
FIG. 2A is a simplified chart showing premature ventricular contraction (PVC) risk versus pacing rate.
Figure 2B:
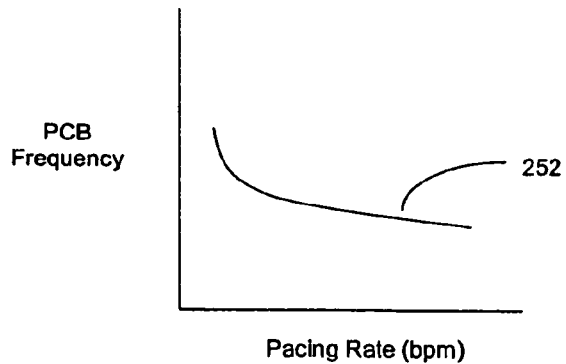
FIG. 2B is a simplified chart showing premature conducted beat (PCB) frequency versus pacing rate.
Figure 2C:
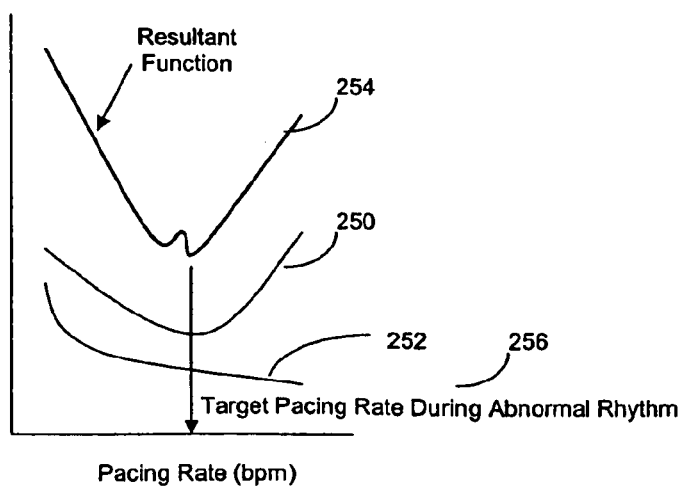
FIG. 2C is a chart showing the resultant function of both PVC risk versus pacing rate and PCB frequency versus pacing rate.

FIGS. 2A, 2B, and 2C illustrate example pacing rate data used in accordance with the invention to determine preferred or optimal pacing rates to be used during normal sinus rhythm and during abnormal rhythm (such as atrial fibrillation), according to an embodiment of the present invention. The invention uses feedback parameters such as heartbeats per minute, number of PVCs, and number of PCBs to determine a preferred or optimal pacing rate for a particular condition. For example, FIG. 2A depicts a function plot 250 of PVC risk versus pacing rate (in beats per minute). While the heart has a normal sinus rhythm, the optimum atrial pacing rate is selected based on minimizing the risk of PVCs. Based on function plot 250, the optimal pacing rate during a normal sinus rhythm is depicted as rate 251.

FIG. 2B depicts a function plot 252 of PCB frequency versus pacing rate (in beats per minute). FIG. 2C depicts, on the same graph, function plots 250 and 252, as well as a resultant function plot 254. The resultant function plot 254 is the sum of function plots 250 and 252. The minimum point on resultant function plot 254 is selected as the optimum pacing rate during an abnormal rhythm, such as atrial fibrillation. Therefore, according to FIG. 2C, the optimum pacing rate during an abnormal rhythm is depicted as rate 256.

A patient is expected to have a changing substrate (i.e., changing condition of the heart), such as the development of myocardial infarction or acute ischemia. This changing substrate may lead to an increased number of PVCs or PCBs. Therefore, the data for function plots 250, 252, and 254 must be updated on a regular basis to keep the optimum pacing rates current.

In this example embodiment, the optimum pacing rate during an abnormal rhythm, such as atrial fibrillation, is the pacing rate that minimizes both the PVC and PCB risk. It will be appreciated by those skilled in the art, however, that minimizing both the PVC and PCB risk may be accomplished via other methods besides summing function plots 250 and 252.

Figure 3:
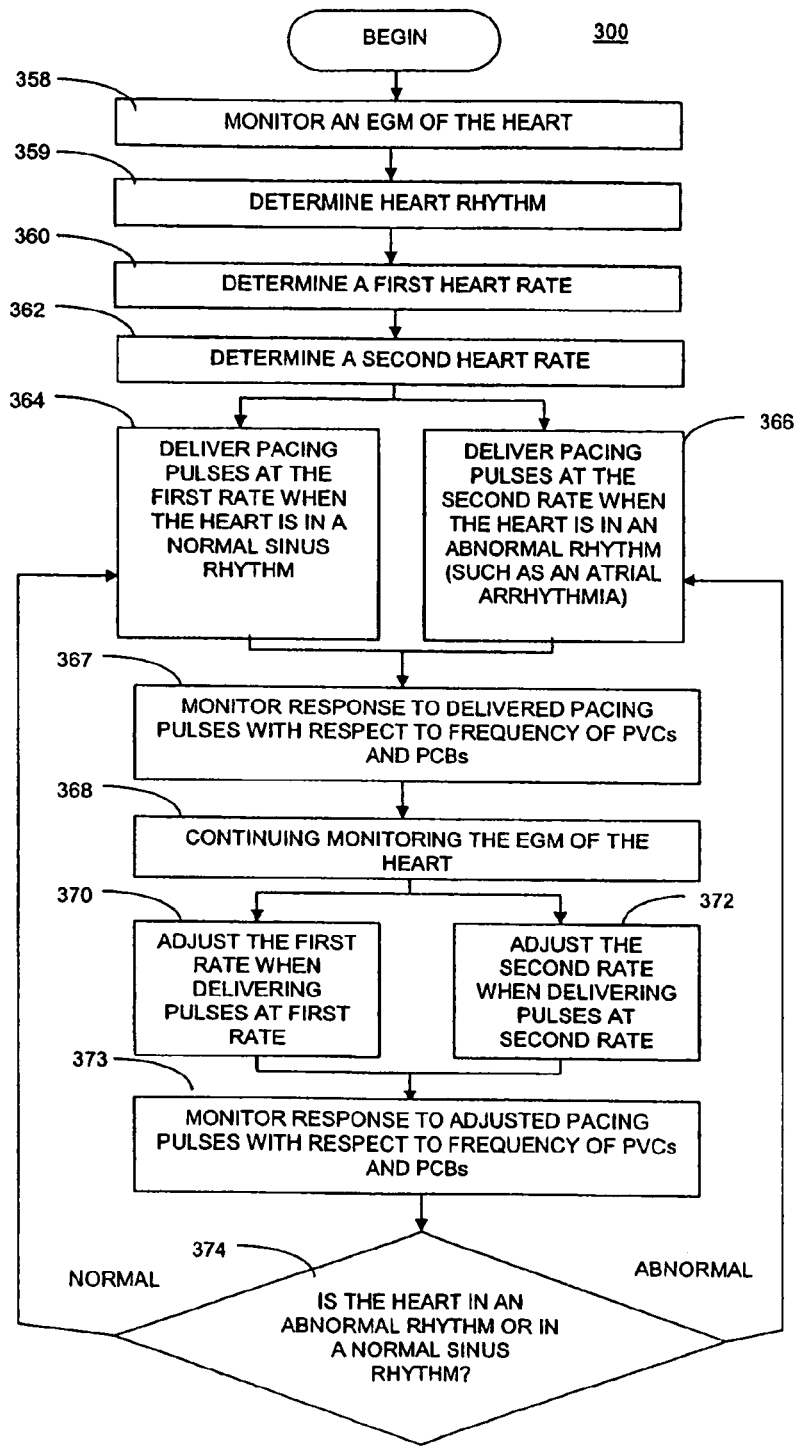
FIG. 3 is a flowchart showing an embodiment of the method of the present invention.

A method 300 of pacing with two arrhythmia prevention modes in accordance with the invention is illustrated in FIG. 3. According to an embodiment of the present invention, the method 300 begins at step 358, in which an EGM of the heart is monitored. Step 358 is a learning phase that will allow the creation of databases, data arrays, data plots or functions, such as function plots 250, 252, and 254 described above, for example. For function plots 250, 252, and 254, the level of PVC risk and the frequency of PCBs are measured as functions of a pacing rate (such as beats per minute (bpm)). The pacing rates tested are from a mean intrinsic rate (e.g., 70 bpm) up to a physiologically acceptable over-drive rate (e.g., 140 bpm), for example.

Figure 4A:
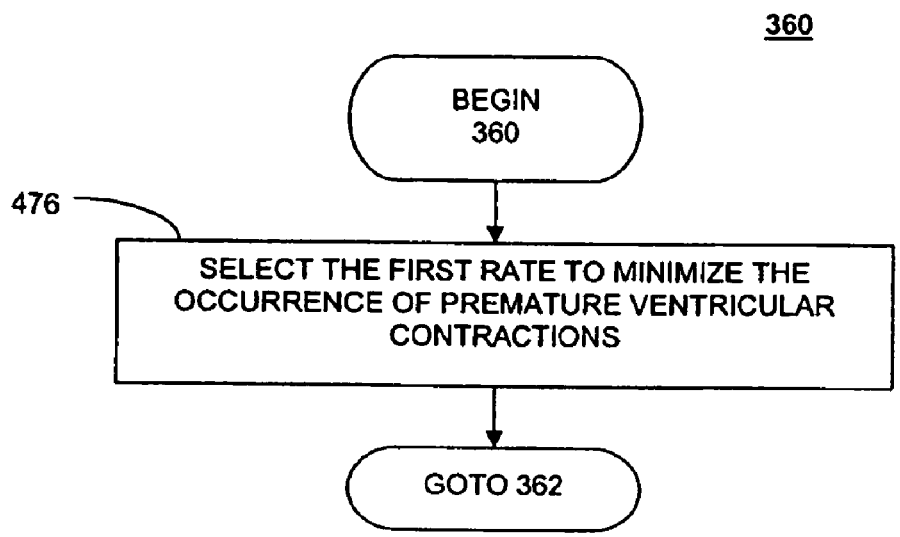
FIG. 4A is a flowchart showing an example of step 360 of FIG. 3 as used in an embodiment of the method of the present invention.
Figure 4B:
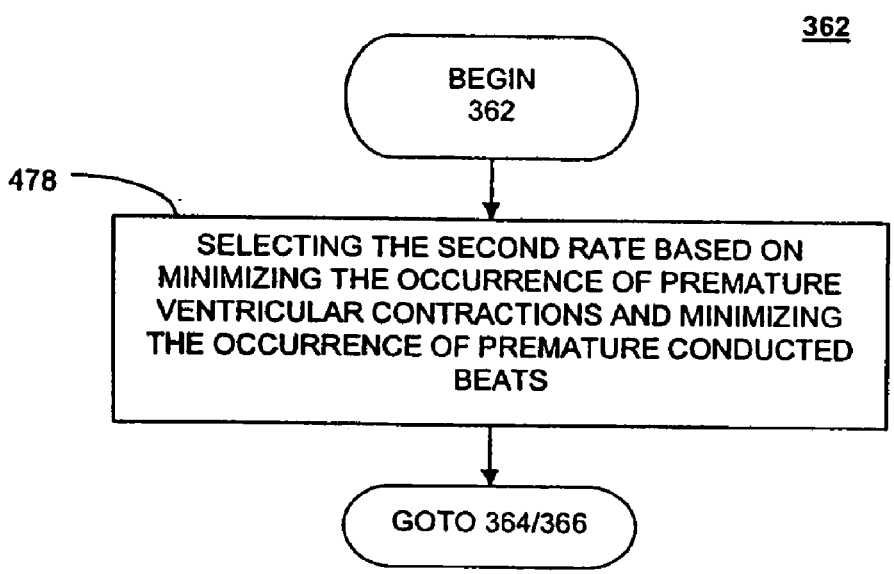
FIG. 4B is a flowchart showing an example of step 362 of FIG. 3 as used in an embodiment of the method of the present invention.

In step 359, it is determined whether the heart is currently in a normal sinus rhythm or in an abnormal rhythm such as an atrial fibrillation or an already present atrial tachyarrhythmia. In step 360, a first heart rate is determined, such as the optimum heart rate for use during a normal sinus rhythm, for example. In one embodiment, step 360 is accomplished by selecting a heart rate to minimize the occurrence of PVCs, as shown in step 476 of FIG. 4A. In the presence of normal sinus rhythm, the optimum heart rate may be associated with atrial pacing, AV sequential pacing, or ventricular pacing. Referring again to FIG. 3, in step 362, a second heart rate is determined, such as the optimum heart rate for use during an abnormal rhythm (atrial fibrillation, for example). In one embodiment, step 362 is accomplished by selecting a heart rate to minimize the occurrence of both PVCs and PCBs, as shown in step 478 of FIG. 4B.

Depending on whether the heart has a normal sinus rhythm or an abnormal rhythm, such as an atrial arrhythmia, the next step is either step 364 or step 366. If the heart has a normal sinus rhythm, paces are delivered at the first rate in step 364. According to an embodiment of the present invention, the paces at the first rate are delivered to an atrium. In another embodiment, the paces at the first rate are delivered to a ventricle. In a further embodiment, the paces at the first rate are delivered to a specified lead of a pacing device. If the heart has an abnormal rhythm, paces are delivered at the second rate in step 366. According to an embodiment of the present invention, the paces at the second rate are delivered to a ventricle. In another embodiment, the paces at the second rate are delivered to a specified lead of a pacing device. Step 367 follows both steps 364 and 366. In step 367, a response to the delivered pacing pulses is monitored with respect to the frequency of PVCs and the frequency of PCBs. In step 368, monitoring the EGM of the heart is continued.

The data functions initially determined in step 358 are preferably updated as monitored EGM data changes. The updated data is then used to adjust the heart rates determined in steps 360 and/or 362. Depending on whether the first rate or the second rate is being used, the next step is either step 370 or step 372. If the first rate is being used, the first rate is adjusted based on monitored EGM data changes in step 370. According to an embodiment of the present invention, the adjustment of the first rate includes re-determining the first rate and delivering pacing pulses at the re-determined first rate. In one embodiment, the first rate is determined by selecting a heart rate to minimize the occurrence of PVCs, as was determined in step 476 of FIG. 4A. If the second rate is being used, the second rate is adjusted based on monitored EGM data changes in step 372. According to an embodiment of the present invention, the adjustment of the second rate includes re-determining the second rate and delivering pacing pulses at the re-determined second rate. In one embodiment, the second rate is determined by selecting a heart rate to minimize the occurrence of both PVCs and PCBs, as was determined in step 478 of FIG. 4B.

Step 373 follows both steps 370 and 372. In step 373, a response to the adjusted pacing pulses is monitored with respect to the frequency of PVCs and the frequency of PCBs. In step 374, it is determined whether the heart has a normal sinus rhythm or an abnormal rhythm, such as an atrial fibrillation. If the heart has a normal sinus rhythm, the method continues at step 364. If the heart has an abnormal rhythm, the method continues at step 366. Thus, in the manner described, the invention monitors an EGM and switches between an arrhythmia prevention mode associated with sinus rhythm and an arrhythmia prevention mode associated with an abnormal rhythm, so that pacing occurs at the optimum rate for the current mode.

Figure 5:
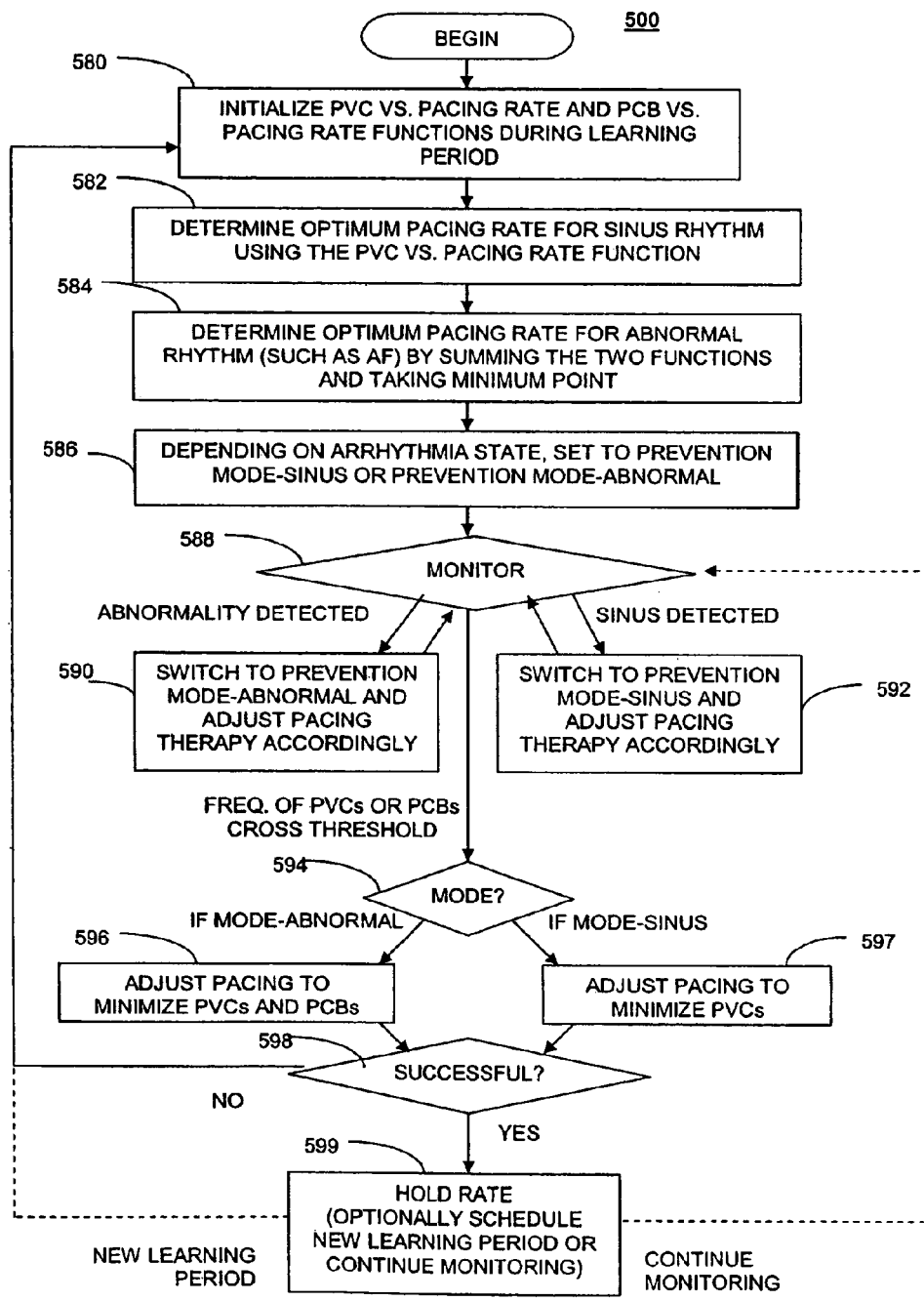
FIG. 5 is a flowchart showing another embodiment of the method of the present invention.

A method 500 of pacing with two arrhythmia prevention modes, according to an embodiment of the present invention, is illustrated in FIG. 5. The method 500 begins at step 580, in which a PVC versus pacing rate function and a PCB versus pacing rate function are initialized during a learning period in which a heart's EGM is Monitored. In step 582, an optimum pacing rate for use during sinus rhythm is determined using the PVC versus pacing rate function by determining the minimum point of the function. In sinus rhythm, while it is helpful to overdrive suppress PVCs, it is also helpful to suppress atrial premature complexes (APCs) in an effort to prevent atrial fibrillation. For more information on atrial fibrillation suppression, see U.S. Pat. No. 6,519,493 to Florio et al., which is incorporated herein by reference. In step 584, an optimum pacing rate for use during an abnormal rhythm, such as atrial fibrillation, is determined by adding the PVC versus pacing rate function and the PCB versus pacing rate function, and determining the minimum point of the resultant function.

In step 586, the mode of the prevention therapy is determined depending on the current arrhythmia state (i.e., sinus rhythm or abnormal rhythm). The appropriate pacing rate determined in step 582 or step 584 is used depending on the mode. In step 588, the heart's EGM is monitored. During heart monitoring, feedback parameters, such as the frequency of PVCs and PCBs, are collected and used to make pacing decisions.

During monitoring step 588, if the current mode is the arrhythmia prevention mode associated with sinus rhythm, but an abnormal arrhythmia is detected (such as atrial fibrillation or other atrial tachyarrhythmia), the method proceeds to step 590. In step 590, the mode is switched from the arrhythmia prevention mode associated with sinus rhythm to the ventricular arrhythmia prevention mode associated with an abnormal rhythm, and the pacing rate is adjusted accordingly. The method then returns to step 588, during which the heart's EGM is again monitored.

During monitoring step 588, if the current mode is the ventricular arrhythmia prevention mode associated with an abnormal rhythm, but a sinus rhythm is detected, the method proceeds to step 592. In step 592, the mode is switched from the ventricular arrhythmia prevention mode associated with an abnormal rhythm to the arrhythmia prevention mode associated with sinus rhythm, and the pacing rate is adjusted accordingly. The method then returns to step 588, during which the heart's EGM is again monitored.

During monitoring step 588, if the frequency of PVCs or PCBs crosses a predetermined threshold, the method proceeds to step 594. In step 594, the current arrhythmia prevention mode is determined. If the current arrhythmia prevention mode is the mode associated with sinus rhythm, the method proceeds to step 597. In step 597, the pacing rate is adjusted to minimize PVCs. If the current arrhythmia prevention mode is the mode associated with an abnormal rhythm, the method proceeds to step 596. In step 596, the pacing rate is adjusted to minimize both PVCs and PCBs. In both steps 596 and 597, the adjustment of the pacing rate begins with the stepping down of the pacing rate, according to an embodiment of the present invention. After steps 596 and 597, the method continues at step 598. In step 598, it is determined whether the pacing rate adjustment of step 596 or 597 was successful. If it was not successful, the method returns to step 580 to re-initialize the PVC versus pacing rate function and the PCB versus pacing rate function during a learning period in which the heart's EGM is monitored. If in step 598 the pacing rate adjustment is determined successful, the method proceeds to step 599. In step 599, the adjusted rate is held. In one embodiment, the method may optionally return to step 580 to schedule a new learning period to re-optimize the pacing rates. In another embodiment, the method may optionally return to step 588 to continue monitoring.

Further information regarding preventive stimulation to prevent tachyarrhythmias can be found in U.S. Pat. No. 6,058,328 to Levine et al. and U.S. Pat. No. 6,292,694 to Schloss et al. The '328 and '694 patents are incorporated herein by reference.

It will be appreciated by those skilled in the art that the above methods 300 and 500 can be used within the hardware, software, and/or firmware of a pacing system, such as the ICD described earlier with reference to FIGS. 1A and 1B, for example.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A method for pacing a heart, comprising:
monitoring an electrogram (EGM) of the heart;
determining whether the heart is in a normal sinus rhythm or in an abnormal rhythm;
determining a level of premature ventricular contraction risk as a function of a pacing rate;
delivering pacing pulses to either an atrium or a ventricle at a first rate to reduce the level of premature ventricular contraction risk when the heart is in a normal sinus rhythm; and
delivering pacing pulses to a ventricle at a second rate to regularize ventricular rhythm when the heart is in an abnormal rhythm.

2. The method of claim 1, further comprising the step of:
monitoring a response to the delivering steps with respect to a frequency of premature ventricular contractions (PVCs) and a frequency of premature conducted beats (PCBs).

3. The method of claim 1, wherein the first and second delivering steps deliver pacing pulses to specified leads of a pacing device.

4. The method of claim 1, wherein the second delivering step comprises:
delivering pacing pulses at the second rate when the heart manifests an atrial arrhythmia.

5. The method of claim 1, further comprising a step after the monitoring step of:
determining the first rate.

6. The method of claim 5, further comprising a step after the monitoring step of:
determining the second rate.

7. The method of claim 6, wherein the first rate determining step comprises:
selecting the first rate to minimize the occurrence of premature ventricular contractions (PVCs).

8. The method of claim 7, wherein the second rate determining step comprises:
selecting the second rate based on minimizing the occurrence of premature ventricular contractions (PVCs) and minimizing the occurrence of premature conducted beats (PCBs).

9. The method of claim 8, further comprising the steps of:
continuing monitoring the electrogram (EGM) of the heart;
adjusting the first rate, when delivering pacing pulses at the first rate; and
adjusting the second rate, when delivering pacing pulses at the second rate.

10. The method of claim 9, further comprising the step of:
monitoring a response to the adjusting steps with respect to a frequency of premature ventricular contractions (PVCs) and a frequency of premature conducted beats (PCBs).

11. The method of claim 9, wherein the first rate adjusting step comprises:
re-determining the first rate; and
delivering pacing pulses at the first rate.

12. The method of claim 11, wherein the first rate re-determining step comprises:
selecting the first rate to minimize the occurrence of premature ventricular contractions.

13. The method of claim 9, wherein the second rate adjusting step comprises:
re-determining the second rate; and
delivering pacing pulses at the second rate.

14. The method of claim 13, wherein the second rate re-determining step comprises:
selecting the second rate based on minimizing the occurrence of premature ventricular contractions and minimizing the occurrence of premature conducted beats.

15. A device for pacing a heart, comprising:
means for monitoring an electrogram (EGM) of the heart;
means for determining whether the heart is in a normal sinus rhythm or in an abnormal rhythm;
means for determining a level of premature ventricular contraction risk as a function of a pacing rate;
means for delivering pacing pulses to either an atrium or a ventricle at a first rate to reduce the level of premature ventricular contraction risk when the heart is in a normal sinus rhythm; and
means for delivering pacing pulses to a ventricle at a second rate to regularize ventricular rhythm when the heart is in an abnormal rhythm.

16. The device of claim 15, further comprising:
means for monitoring a response to the delivered pacing pulses with respect to a frequency of premature ventricular contractions (PVCs) and a frequency of premature conducted beats (PCBs).

17. The device of claim 15, wherein the first and second delivering means deliver pacing pulses to specified leads of a pacing device.

18. The device of claim 15, wherein the second delivering means comprises:
means for delivering pacing pulses at the second rate when the heart manifests an atrial arrhythmia.

19. The device of claim 15, further comprising:
means for determining the first rate.

20. The device of claim 19, further comprising:
means for determining the second rate.

21. The device of claim 20, wherein the means for determining the first rate comprises:
   means for selecting the first rate to minimize the occurrence of premature ventricular contractions.

22. The device of claim 21, wherein the means for determining the second rate comprises:
   means for selecting the second rate based on minimizing the occurrence of premature ventricular contractions and minimizing the occurrence of premature conducted beats.

23. The device of claim 22, further comprising:
   means for continuing monitoring the electrogram (EGM) of the heart;
   means for adjusting the first rate, when delivering pacing pulses at the first rate; and
   means for adjusting the second rate, when delivering pacing pulses at the second rate.

24. The device of claim 23, further comprising:
   means of monitoring a response to the adjusted rates with respect to a frequency of premature ventricular contractions (PVCs) and a frequency of premature conducted beats (PCBs).

25. The device of claim 23, wherein the first adjusting means comprises:
   means for re-determining the first rate; and
   means for delivering pacing pulses at the first rate.

26. The device of claim 25, wherein the re-determining means comprises:
   means for selecting the first rate to minimize the occurrence of premature ventricular contractions.

27. The device of claim 23, wherein the second adjusting means comprises:
   means for re-determining the second rate; and
   means for delivering pacing pulses at the second rate.

28. The device of claim 27, wherein the re-determining means comprises:
   means for selecting the second rate based on minimizing the occurrence of premature ventricular contractions and minimizing the occurrence of premature conducted beats.

29. A method for pacing a heart, comprising:
   monitoring an electrogram (EGM) of the heart;
   determining whether the heart is in a normal sinus rhythm or in an abnormal rhythm;
   determining a level of premature ventricular contraction risk and occurrence of premature conducted beats as a function of a pacing rate;
   selecting a first rate to minimize the occurrence of premature ventricular contractions (PVCs);
   selecting a second rate based on minimizing the occurrence of premature ventricular contractions (PVCs) and minimizing the occurrence of premature conducted beats (PCBs);
   delivering pacing pulses at the first rate when the heart is in a normal sinus rhythm; and
   delivering pacing pulses at the second rate when the heart is in an abnormal rhythm.

* * * * *